(12) United States Patent
Criscuolo et al.

(10) Patent No.: US 8,821,522 B2
(45) Date of Patent: Sep. 2, 2014

(54) HERNIA MESH TACKS

(71) Applicant: Covidien LP, Mansfield, MA (US)

(72) Inventors: Christopher J. Criscuolo, Brandford, CT (US); Ernie Aranyi, Easton, CT (US)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 13/744,699

(22) Filed: Jan. 18, 2013

(65) Prior Publication Data

US 2013/0131700 A1 May 23, 2013

Related U.S. Application Data

(63) Continuation of application No. 12/818,541, filed on Jun. 18, 2010, now Pat. No. 8,382,778, which is a continuation of application No. 10/517,402, filed as application No. PCT/US03/18739 on Jun. 11, 2003, now Pat. No. 7,867,252.

(60) Provisional application No. 60/388,119, filed on Jun. 11, 2002.

(51) Int. Cl.
*A61B 17/08* (2006.01)

(52) U.S. Cl.
USPC ........... 606/151; 606/232; 606/300; 606/301; 606/304; 606/305; 411/378; 411/413

(58) Field of Classification Search
CPC ................... A61B 17/88; A61B 17/68; A61B 2017/0648; A61B 17/8625; A61B 17/888; A61B 17/064; A61B 17/10; A61B 17/08; A61F 2/0063

See application file for complete search history.

(56) References Cited

U.S. PATENT DOCUMENTS

| 373,074 A | 11/1887 | Jones |
|---|---|---|
| 2,167,558 A | 7/1939 | Upson |

(Continued)

FOREIGN PATENT DOCUMENTS

| EP | 1 025 803 A1 | 8/2000 |
|---|---|---|
| EP | 1 293 168 A2 | 3/2003 |

(Continued)

OTHER PUBLICATIONS

International Search Report corresponding to European Application No. EP 08004478; date of mailing is May 16, 2008; date of completion is May 2, 2008; 8 pages.

(Continued)

*Primary Examiner* — Corrine M McDermott
*Assistant Examiner* — Son Dang

(57) ABSTRACT

There are disclosed various embodiments of surgical tacks for use in surgical procedures. The tacks generally include a head and a barrel portion extending distally from the head. Preferably, the head and the barrel portion define a throughbore for receipt of a drive instrument. A thread on the head is provided to engage threads in the installation tool. A tissue thread is provided on the barrel portion to engage tissue. Distal and proximal surfaces of the tissue thread may be oriented at various angles relative to the barrel portion. There is also disclosed an insertion instrument to insert one or more tacks as well as a method of use. There is further disclosed a model device for use in explaining the operation of the instrument.

15 Claims, 15 Drawing Sheets

(56) References Cited

U.S. PATENT DOCUMENTS

| | | |
|---|---|---|
| 3,233,500 A | 2/1966 | De Vellier |
| 3,357,094 A * | 12/1967 | Mouck ............................ 29/509 |
| 4,456,005 A | 6/1984 | Lichty |
| 4,507,817 A | 4/1985 | Staffeld |
| 4,532,926 A | 8/1985 | O'Holla |
| 4,740,123 A | 4/1988 | Wollar et al. |
| 4,844,606 A | 7/1989 | Smith |
| 4,924,865 A | 5/1990 | Bays et al. |
| 4,976,715 A | 12/1990 | Bays et al. |
| 5,015,134 A | 5/1991 | Gotoh |
| 5,019,079 A | 5/1991 | Ross |
| 5,053,036 A | 10/1991 | Perron et al. |
| 5,129,906 A | 7/1992 | Ross et al. |
| 5,169,400 A | 12/1992 | Muhling et al. |
| 5,300,076 A | 4/1994 | Leriche |
| 5,354,292 A | 10/1994 | Braeuer et al. |
| 5,375,956 A | 12/1994 | Pennig |
| 5,456,685 A | 10/1995 | Huebner |
| 5,464,427 A | 11/1995 | Curtis et al. |
| 5,536,127 A | 7/1996 | Pennig |
| 5,728,116 A | 3/1998 | Rosenman |
| 5,730,744 A | 3/1998 | Justin et al. |
| 5,743,914 A | 4/1998 | Skiba |
| 5,797,914 A | 8/1998 | Leibinger |
| 5,840,078 A | 11/1998 | Yerys |
| 5,891,146 A | 4/1999 | Simon et al. |
| 5,968,047 A | 10/1999 | Reed |
| 5,971,985 A | 10/1999 | Carchidi et al. |
| 6,001,101 A | 12/1999 | Augagneur et al. |
| 6,030,162 A | 2/2000 | Huebner |
| 6,042,314 A | 3/2000 | Guelck |
| 6,053,918 A | 4/2000 | Spievack |
| 6,096,060 A | 8/2000 | Fitts et al. |
| 6,117,162 A | 9/2000 | Schmieding et al. |
| 6,158,938 A | 12/2000 | Savoji |
| 6,231,606 B1 | 5/2001 | Graf et al. |
| 6,306,140 B1 | 10/2001 | Siddiqui |
| 6,319,254 B1 | 11/2001 | Giet et al. |
| 6,319,270 B1 | 11/2001 | Grafton et al. |
| 6,368,322 B1 | 4/2002 | Luks et al. |
| 6,402,757 B1 | 6/2002 | Moore, III et al. |
| 6,503,251 B1 | 1/2003 | Shadduck |
| 6,632,245 B2 | 10/2003 | Kim |
| 6,908,466 B1 | 6/2005 | Bonutti et al. |
| 6,979,163 B2 | 12/2005 | Brletich et al. |
| 2001/0004694 A1 | 6/2001 | Carchidi |
| 2001/0007074 A1 | 7/2001 | Strobel et al. |
| 2003/0036755 A1 | 2/2003 | Ginn |
| 2003/0082026 A1 | 5/2003 | Brletich et al. |
| 2003/0099102 A1 | 5/2003 | Duval |
| 2004/0204723 A1 | 10/2004 | Kayan |
| 2004/0215333 A1 | 10/2004 | Duran et al. |
| 2004/0254608 A1 | 12/2004 | Huitema et al. |
| 2006/0124688 A1 | 6/2006 | Racenet et al. |
| 2006/0273135 A1 | 12/2006 | Beetel |
| 2006/0291981 A1 | 12/2006 | Viola et al. |
| 2007/0250064 A1 | 10/2007 | Darois et al. |
| 2009/0311074 A1 | 12/2009 | Friederich et al. |

FOREIGN PATENT DOCUMENTS

| | | |
|---|---|---|
| JP | 09149906 | 6/1997 |
| WO | WO 01/62136 A1 | 8/2001 |
| WO | WO 01/97677 A2 | 12/2001 |
| WO | WO 02/30296 A2 | 5/2002 |
| WO | WO 02/091932 A1 | 11/2002 |
| WO | WO 03/034925 A2 | 5/2003 |
| WO | WO 03/049906 A1 | 6/2003 |

OTHER PUBLICATIONS

International Search Report corresponding to European Application No. EP 04755078; date of mailing is Jul. 2, 2008; date of completion is Jun. 20, 2008; 4 pages.

International Search Report corresponding to European Application No. EP 08251988; date of mailing is Oct. 17, 2008; date of completion is Sep. 19, 2008; 3 pages.

International Search Report corresponding to International Application No. PCT/US03/18739; date of mailing is Feb. 26, 2004; date of completion is Feb. 18, 2004; 5 pages.

\* cited by examiner

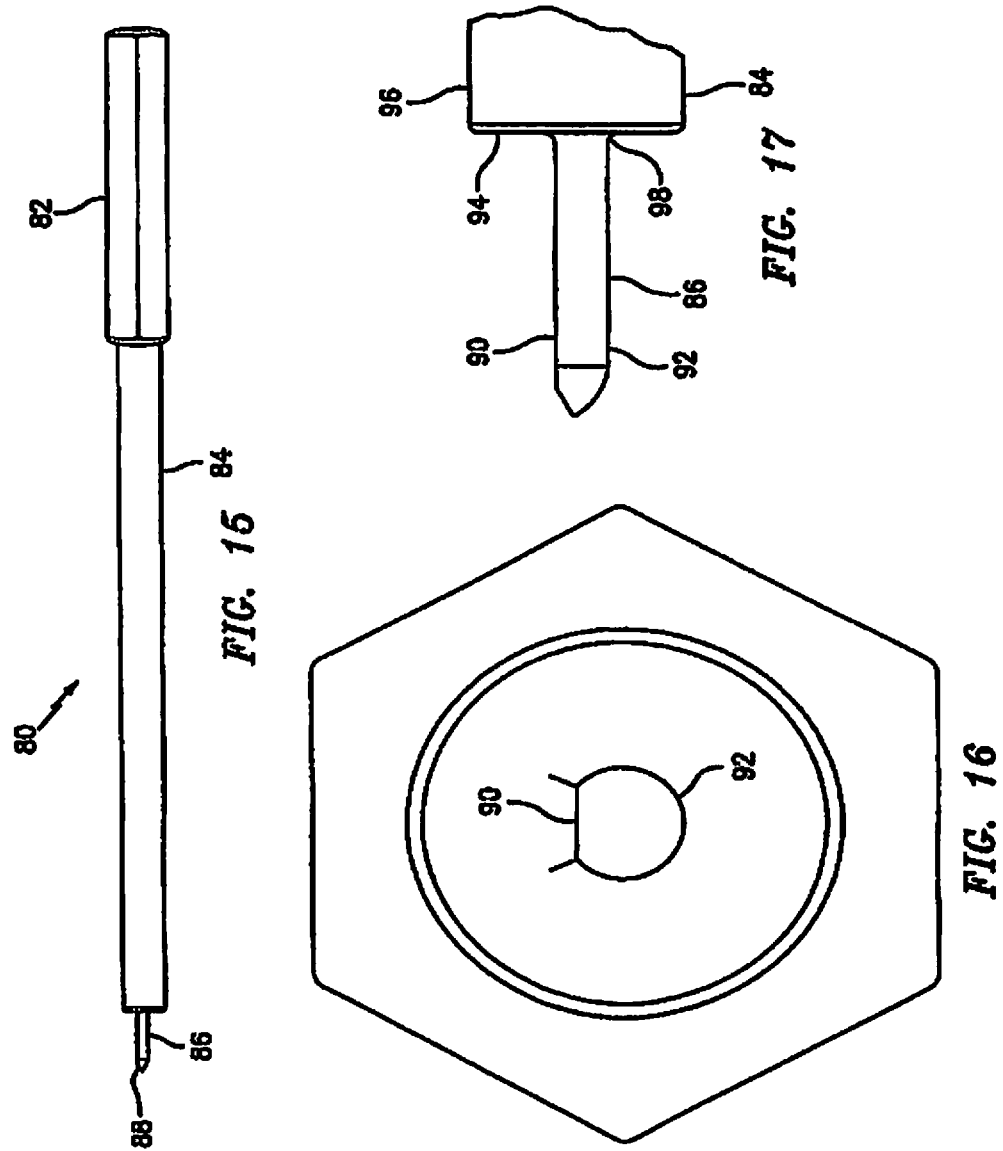

HERNIA MESH TACKS

CROSS-REFERENCE TO RELATED APPLICATIONS

This application is a continuation of U.S. patent application Ser. No. 12/818,541, filed Jun. 18, 2010, which is a continuation of U.S. patent application Ser. No. 10/517,402, filed on Dec. 7, 2004, now U.S. Pat. No. 7,867,252, which is a U.S. National Stage Application filed under 35 U.S.C. §371 (a) of International Application Serial No. PCT/US2003/018739, filed on Jun. 11, 2003, which claims the benefit of and priority to U.S. Provisional Patent Application Ser. No. 60/388,119 filed Jun. 11, 2002, the entire contents of each of these prior applications being incorporated by reference herein.

BACKGROUND

1. Technical Field

The technical field relates to surgical tacks for use in securing mesh during a hernia repair procedure and, more particularly, to absorbable surgical tacks and insertion instruments.

2. Background of Related Art

During hernia repair surgery, it is often necessary to affix a section of mesh over the herniated tissue. This is often accomplished through the use of staples or sutures or other affixation type means.

One method of affixing mesh to tissue is through the use of surgical screws or tacks. However, known tacks may have a traumatic distal end which causes damage to the hernia mesh and unnecessarily injures the tissue as the tack is being inserted. Furthermore, many of these tacks are not configured to be removed after they have been implanted in the patient. Thus, it would be desirable to provide an absorbable hernia tack capable of a traumatic insertion through mesh and into tissue and having sufficient tissue surface bearing area to solidly retain the mesh against the tissue.

It would also be desirable to have a hernia tack which is capable of being removed by means of the insertion tool.

SUMMARY

There are disclosed absorbable hernia tacks suitable for use in securing hernia mesh against tissue. The tacks generally include a barrel portion having a head extending distally therefrom. The barrel portion and the head define a throughbore for receipt of a drive rod of an insertion instrument so that the hernia tack can be driven through mesh and into tissue. The throughbore may have various non-circular shapes, such as D-shaped, rectangular, polygonal, etc., to increase the drive surface area and facilitate insertion in tough tissue. A tissue thread is formed on the barrel portion and is configured to engage tissue as the tack is rotated into the tissue. The tissue thread includes a leading edge at the distal end of the barrel portion and a trailing edge at a proximal end of the barrel portion. The leading edge has the advantage of following a tip of an insertion tool to allow a traumatic entry of the tack into tissue.

The head is provided with a drive thread which is configured to engage an inner surface of an insertion tool and allow the tack to be moved distally within the insertion tool as the drive rod is rotated. The drive thread has a leading edge at its distal end and a trailing edge at its proximal end. Preferably, these surfaces are chamfered or rounded off so as to facilitate engagement with the insertion tool. The throughbore of the hernia tack can have various configurations to mate with a drive rod of an insertion tool. In one embodiment, the throughbore of the hernia tack has essentially a D-shaped cross sectional area. However, other cross sectional areas may be provided for example, a rectangular cross section or polygonal cross section.

In various embodiments of the surgical tacks, the proximal and distal surfaces of the tissue thread may form various acute or obtuse angles relative to the barrel portion. These angles provide the advantages of increasing the hold of the thread in tissue and allowing for easier insertion and/or removal of the tack from tissue. Alternatively, one or more of these surfaces may be perpendicular to the barrel portion. It should be noted that the drive thread has a substantially greater diameter than the tissue thread to allow the head to seat against the mesh without entering the hole in the mesh formed by the barrel and tissue thread. The drive thread and the tissue thread are not connected that is, i.e., are discontinuous with respect to each other to achieve this advantage.

There is also disclosed an insertion tool for inserting one or more hernia tacks through mesh and into tissue. The insertion tool generally includes an elongated outer tube which is affixed at its distal end to a handle mechanism. The insertion tool also includes an inner drive rod which is rotatably connected to the handle mechanism. A pointed tip of the drive rod forms an atraumatic transition with the atraumatic tip of the barrel portion to prevent tearing mesh and tissue as the tack is inserted therethrough. Various known handle mechanisms may be utilized to rotate the inner drive rod with respect to the stationary outer tube. An inner thread may be provided within the outer tube so as to engage the drive thread of the head of the hernia tack. Preferably, the distal end of the inner thread is flush with the distal end of the outer tube so that in the event a tack need be removed, the insertion tool may be positioned over the drive cap of the tack and rotated in an opposite direction to draw the tack back into the insertion tool and thereby remove the tack from the body.

The inner thread may be provided only at a distal end of the outer tube or may be provided throughout the entire length of the outer tube. When the drive thread is provided throughout the entire length of the drive tube no biasing spring need be necessary to force additional tacks distally as they are moved distally along the thread as the drive rod is rotated. However, in the event the inner thread is only provided at the distal end, various other known means may be utilized to bias subsequent tacks distally towards the inner thread.

There is also disclosed a display model of any insertion tool and hernia tack which may be utilized for instructional purposes to demonstrate to surgeons how the hernia tack and insertion tools work. This is necessary due to the extremely small nature of the tacks which are generally on the order of only a few millimeters in diameter. The display model includes a mock outer tube having an inner thread along with a drive rod having an end cap. A sample hernia tack is also provided. The outer tube and head cap/drive rod are separable to drop the tack into the proximal end of the model. Thereafter the D-shaped drive rod is positioned within the D-shaped throughbore of the tack and the head cap rotated to rotate the tack out the distal end of the outer tube.

BRIEF DESCRIPTION OF THE DRAWINGS

Various embodiments are described herein with reference to the drawings wherein:

FIG. 15 is a side view of a single tack drive rod;

FIG. 16 is an end view of the rod of FIG. 15;

FIG. 17 is an enlarged side view of the distal end of the rod of FIG. 15;

DETAILED DESCRIPTION OF PREFERRED EMBODIMENTS

Figure 1:
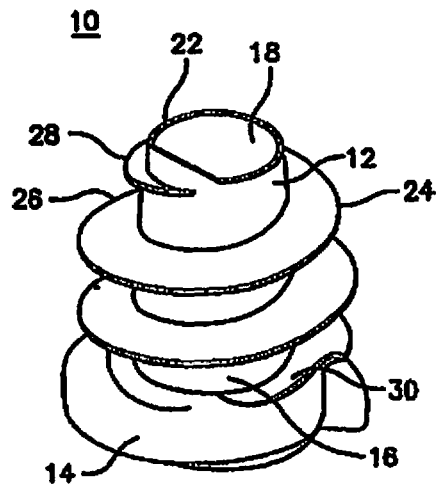
FIG. 1 is a perspective view of a first embodiment of a hernia repair tack.
Figure 2:
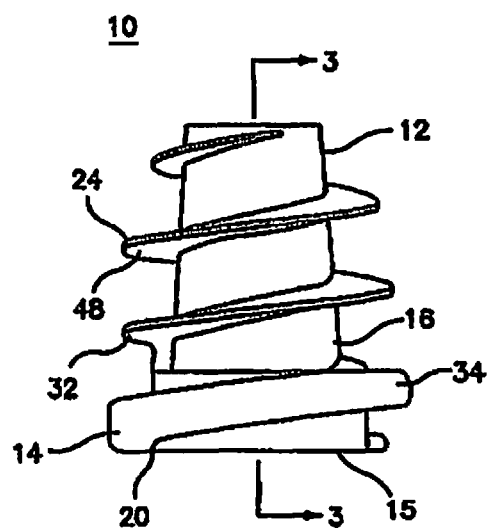
FIG. 2 is a side view of the hernia repair tack.

Referring to FIGS. 1 and 2, there is disclosed a hernia tack suitable for atraumatic insertion through hernia mesh and into human tissue. Hernia tack 10 generally includes an elongated barrel portion 12 having a cap or head 14 at a proximal end 16 of barrel portion 12. Barrel portion 12 extends distally from head 14 and is preferably tapered. A detent may be formed in a proximal surface 15 of head 14 for receipt of driving instrumentation. Preferably, barrel portion 12 and head cap 14 define a throughbore 18 therethrough. Throughbore 18 extends from a proximal end 20 of head cap 14 to a distal end 22 of barrel portion 12.

Preferably, distal end 22 is smooth or rounded off to avoid traumatizing tissue and damaging the mesh as tack 10 is installed. Distal end 22 forms an atraumatic transition with the tip of a drive rod to prevent tearing of mesh and tissue during insertion. Tack 10 can be formed of any biocompatible material and preferably of a material that is absorbable. In order to facilitate insertion and retention of hernia tack 10 in tissue, barrel portion 12 is provided with a tissue thread 24 having a leading edge 26 at a distal end 28 of tissue thread 24 and a trailing edge 30 at a proximal end 32 of tissue thread 24. The use of a tissue thread in a hernia mesh tack allows for a larger surface bearing area against tissue to prevent pulling out of tissue. This is a clear advantage over prior art types of tacks. Leading edge 26 of tissue thread 24 tapers toward distal end 22 of barrel portion 12 to facilitate rotating tack 10 through hernia mesh and a tissue puncture made with a drive instrument discussed as discussed more fully hereinbelow.

In order to utilize hernia tack 10 with a suitable drive instrument, head 14 is provided with a drive thread 34. Drive thread 34 has a leading edge 36 at a distal end 38 of drive thread 34 and a trailing edge 40 at a proximal end 42 of drive thread 34. The maximum diameter of drive thread 34 is greater than the maximum diameter of tissue thread 24 so that as tack 10 is rotated through a drive instrument tissue thread 24 does not contact the drive instrument and thread 24 is not damaged.

Figure 5:
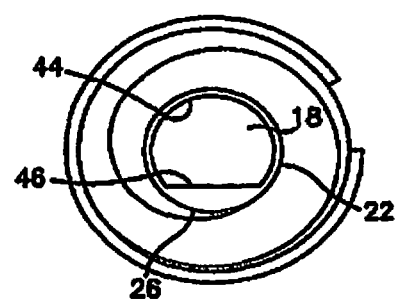
FIG. 5 is a distal end view of the tack.
Figure 4:
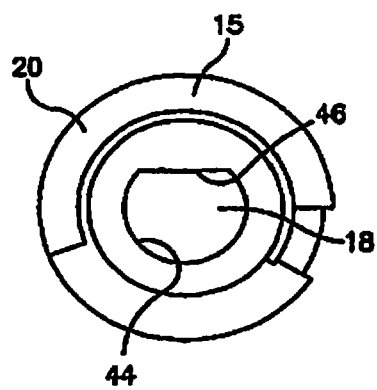
FIG. 4 is a proximal end view of the tack.

Referring to FIGS. 4 and 5, a drive instrument, described hereinbelow, is configured to pass a drive rod into the detent in head 14 or through throughbore 18 and rotate tack 10. As shown, throughbore 18 has an arcuate portion 44 and a flat portion 46 which combine to form a generally D-shaped throughbore. This allows a similarly shaped drive rod to engage inner surface of throughbore 18 and rotate tack 10.

Figure 7:
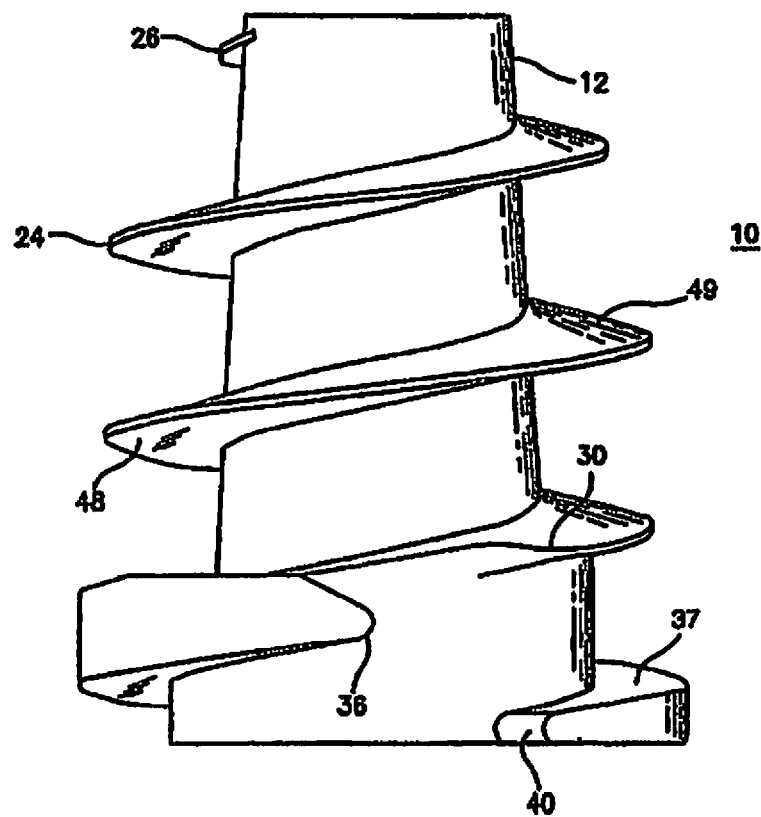
FIG. 7 is a side view of the tack.

Tissue thread 24 has a proximal surface 48 which is oriented approximately perpendicularly or at a 90° angle to barrel portion 12. This provides a generally flat surface area to engage tissue to avoid pulling out of tack 10 from tissue. Referring for the moment to FIG. 7, a distal face 49 of thread 24 forms and obtuse angle with barrel portion 12 to facilitate insertion of tack 10.

Figure 3:
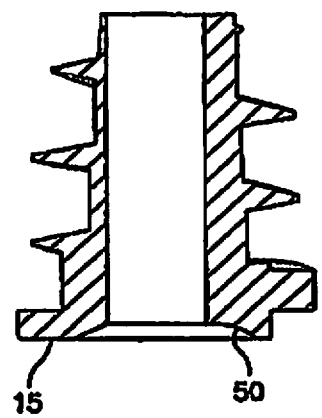
FIG. 3 is a side sectional view taken along the line 3-3 of FIG. 2.

As shown in FIG. 3, a proximal end of head 14 has a chamfered surface 50 to facilitate receipt of insertion tools, such as a drive rod, in throughbore 18.

Figure 6:
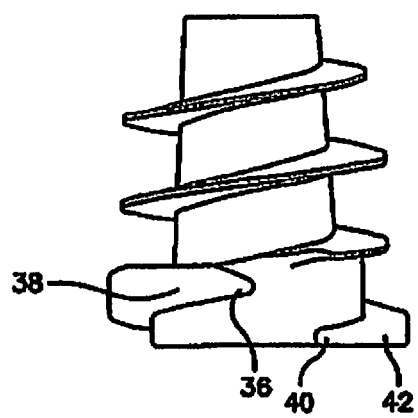
FIG. 6 is a perspective view of the tack, similar to that of FIG. 2, with the tack rotated 180.

Referring now to FIGS. 6 and 7, drive thread 34 is more clearly illustrated. As shown, leading edge 36 and trailing edge 40 of drive thread 34 are rounded so as to facilitate ease of insertion in a drive apparatus. Further, trailing edge 40 is flush with a proximal surface 15 of head 14 to facilitate reengagement of tack 10 by an insertion instrument to facilitate removal of tack 10.

Figure 8:
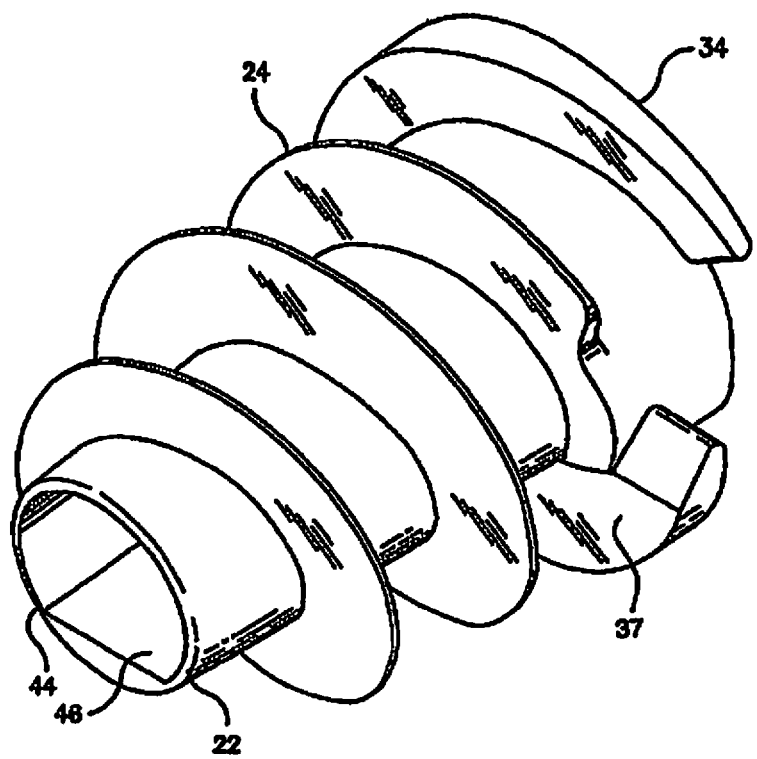
FIG. 8 is a perspective view of the tack illustrating the through bore.

Referring to FIGS. 7 and 8, it can be seen that trailing edge 30 of tissue thread 24 and leading edge 36 of drive thread 34 are discontinuous and do not form one continuous thread. In particular, a tapered edge 37 of drive thread 34 prevents drive thread 34 from continuing into tissue after trailing edge 30 of tissue thread 24 is fully inserted in the tissue. FIG. 8 also shows the D-shaped throughbore 18.

Figure 9:
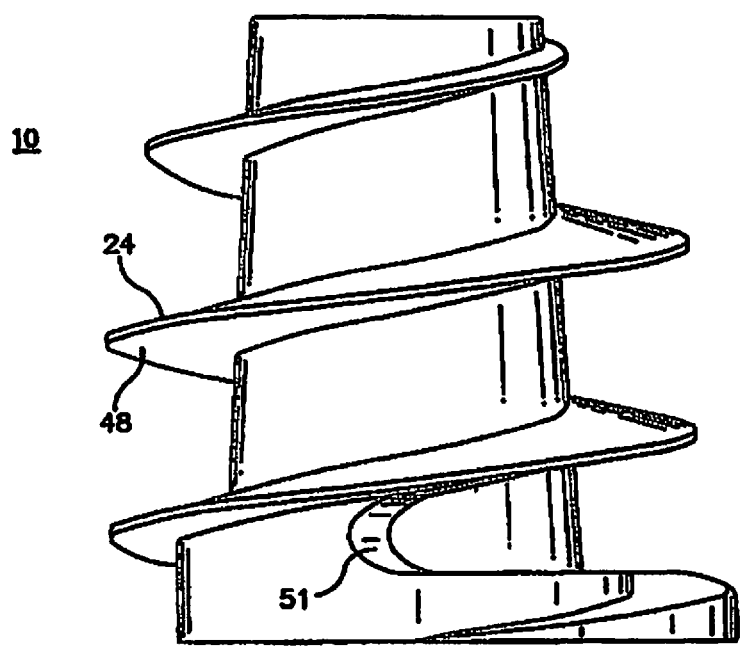
FIG. 9 is a side view of the tack similar to FIG. 7, rotated 180.

FIG. 9 illustrates the generally flat proximal surface 48 of tissue thread 24 as well as the transition zone 51 between tissue thread 24 and drive thread 34.

Figure 10:
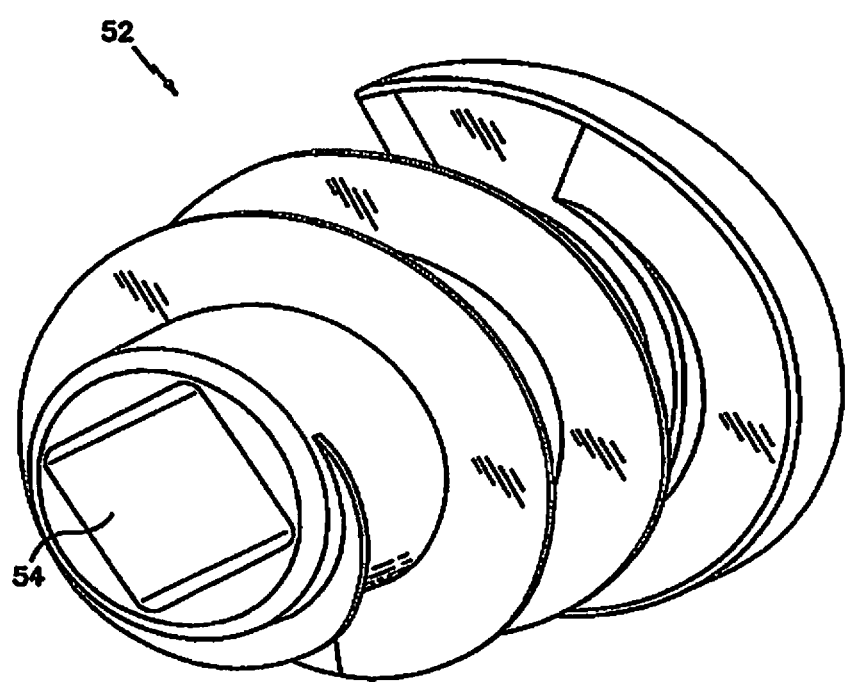
FIG. 10 is a perspective view of a tack illustrating an alternate through bore.
Figure 11:
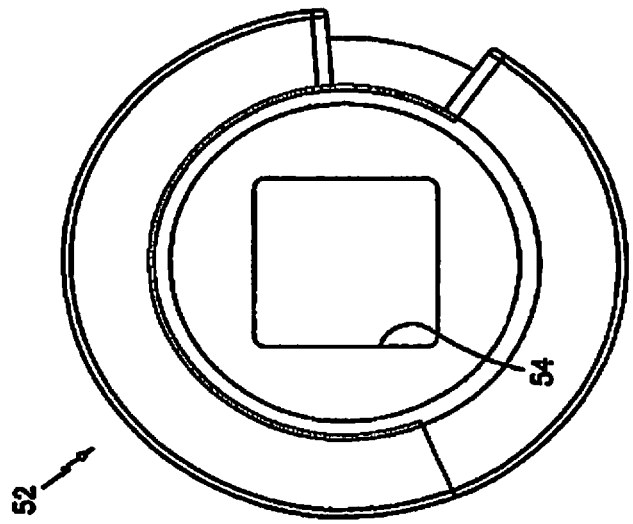
FIG. 11 is an end view of the tack of FIG. 10.

Referring now to FIGS. 10 and 11 there is illustrated an alternative embodiment of a hernia tack 52 which in most respects is the same as hernia tack 10. However, hernia tack 52 includes a square shaped throughbore 54 for engagement with a different style drive apparatus. The square shape of throughbore 54 provides more surface area for the insertion tool to engage. This may aid in driving tack 52 into tough tissues without possibility of stripping throughbore 54.

Figure 12:
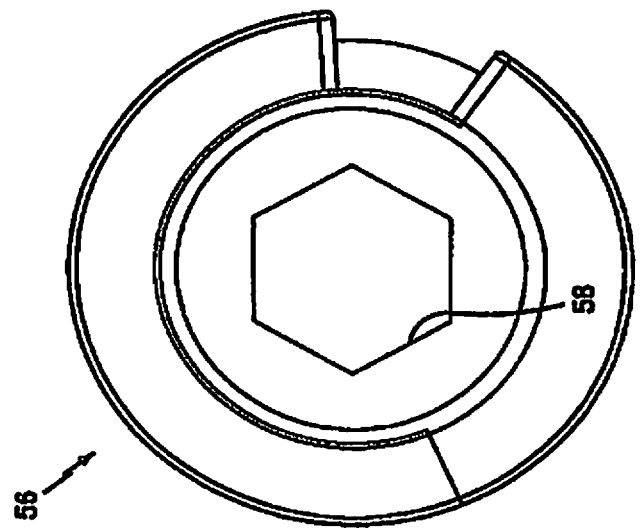
FIG. 12 is an end view of a tack having a further alternate through bore.

Similarly, referring now to FIG. 12, there is illustrated an end view of an alternative tack 56 which has a polygonal shaped throughbore 58 to provide yet more surface area for engagement with insertion instrumentation. Various other throughbore shapes, such as, for example, oval, star shaped, etc. may be provided to operate with various insertion instruments. Any non-circular shape for the cross section of the throughbore is contemplated herein.

Figure 13:
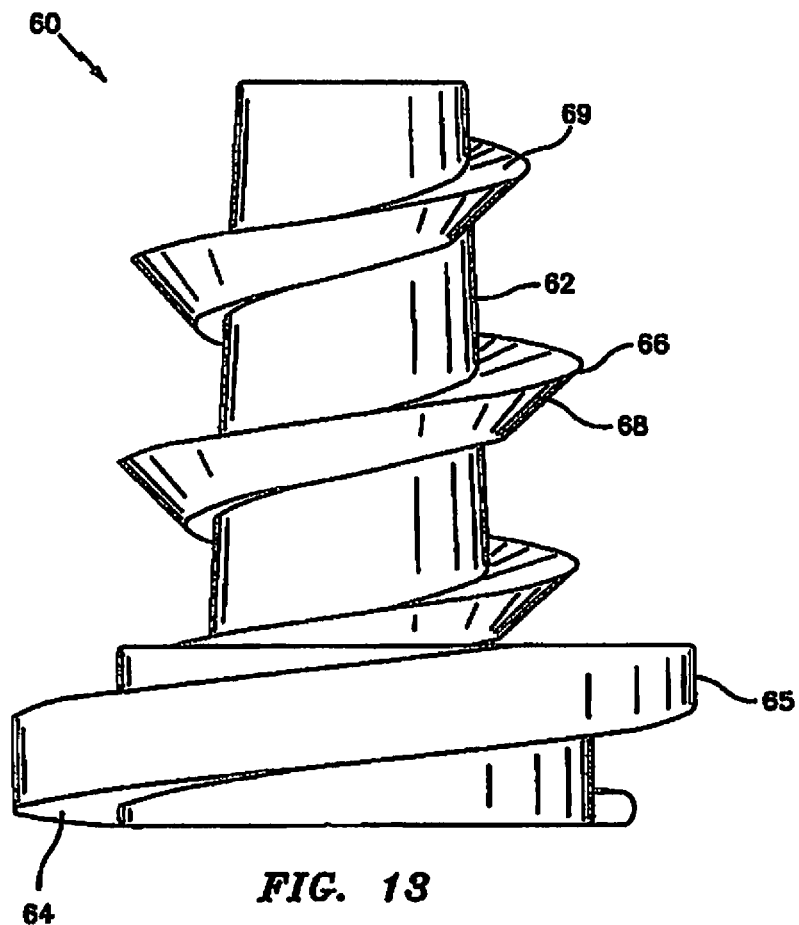
FIG. 13 is a perspective view of an alternate embodiment of a tack.

Referring now to FIG. 13, there is disclosed an alternative embodiment of a surgical tack having a differing style tissue thread. Tack 60 generally includes a barrel portion 62 and a head 64. Head 64 has a drive thread 65 to engage threads in an insertion tool. In this embodiment of tack 60, a proximal surface 68 of a tissue thread 66 generally forms an obtuse angle with respect to barrel portion 62. This angle of tissue thread 66 may assist in those situations where tack 60 needs to be removed or backed out of the tissue and the mesh. A distal surface 69 of thread 66 may be oriented substantially perpendicular to barrel portion 62 as shown. While not specifically shown, either or both of proximal surface 68 and distal surface 69 of tissue thread 66 may form an angle of less than 90 degrees with barrel portion 62 to aid in anchoring tack 60 within tissue.

Figure 14:
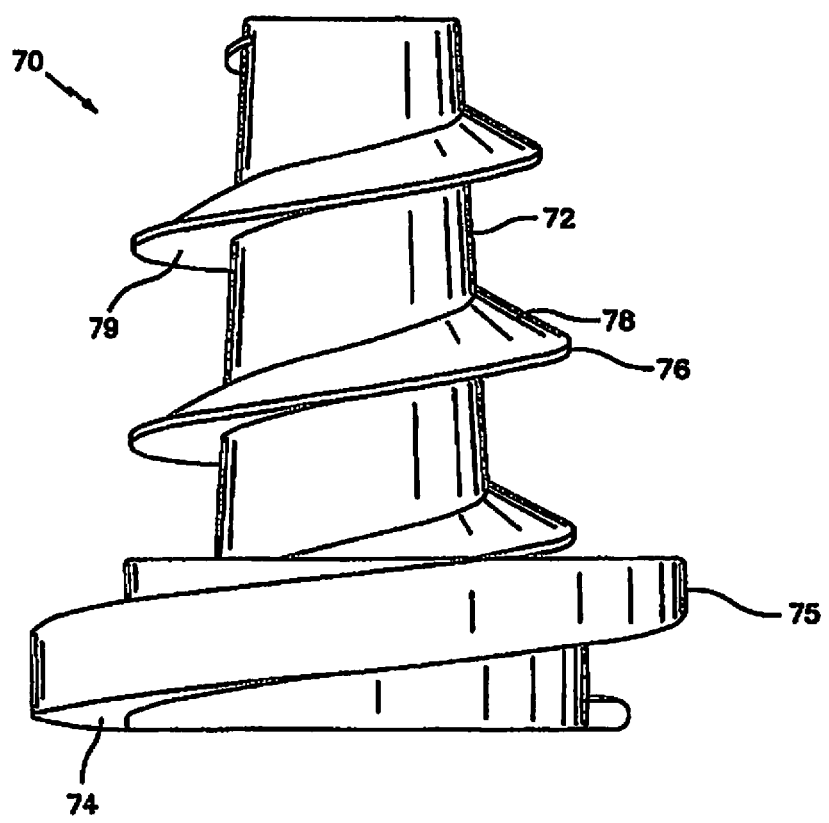
FIG. 14 is a perspective view of a further alternate embodiment of a tack.

Referring now to FIG. 14, there is disclosed a further alternative embodiment of a surgical tack. Tack 70 is similar to tacks 10 and 60 hereinabove and generally includes a barrel portion 72 having a head 74. Head 74 has a drive thread 75 to engage the threads in an insertion instrument. Tissue thread 76 formed on body portion 72 includes a distal surface 78 which forms an obtuse angle with barrel portion 72. This may assist in driving tack 70 through the mesh and into the tissue. As shown, a proximal surface 79 of tissue thread 76 may be oriented perpendicular to barrel portion 72.

Referring now to FIG. 15 there is illustrated a drive rod 80 for use in a tack applying instrument. Drive rod 84 is utilized in those insertion tools which are configured to apply a single tack to hernia mesh and tissue. Drive rod 80 generally includes a proximal end section 82 configured to be engaged by an actuation mechanism of a surgical instrument such that actuation of the instrument rotates drive rod 80. Drive rod 80 also includes a center section 84 extending distally from proximal end section 82 and a distal section 86 extending distally from center section 84. Preferably, distal section 86 terminates in a sharp tissue penetrating tip 88.

Figure 18:
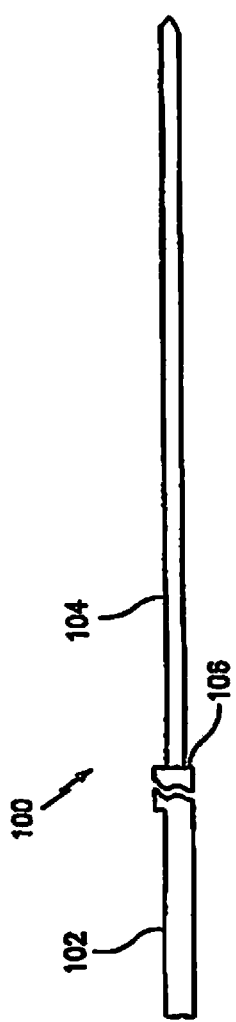
FIG. 18 is a side view of a multi-tack drive rod.

As best shown in FIGS. 16 and 17, distal section 86 of drive rod 80 includes a flat portion 90 and an arcuate portion 92 which forms a generally D-shape so as to engage the generally D-shaped throughbore of a tack. As best shown in FIG. 18, an abutment surface 94 is formed between a distal end 96 of center section 84 and a proximal end 98 of distal section 86. This abutment surface 94 is configured to engage the proximal surface of the head of the tack.

Figure 20:
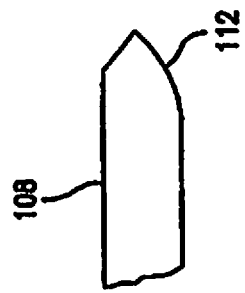
FIG. 20 is an enlarged side view of the distal end of the rod of FIG. 18.
Figure 19:
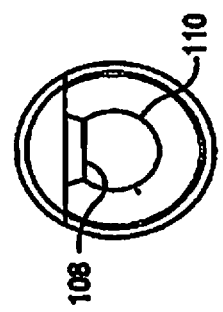
FIG. 19 is an end view of the rod of FIG. 18.

Referring now to FIGS. 18-20, and initially with respect to FIG. 18, there is illustrated drive rod 100 for use with multiple tacks. Drive rod 100 generally includes a proximal section 102 and a distal section 104. An abutment surface 106 is formed between distal section 104 and proximal section 102 to engage a tack. Distal section 104 sufficiently elongate so as to receive multiple tacks therealong.

Referring to FIG. 19, distal section 104 includes a flat surface 108 and an arcuate surface 110 which is configured to engage the throughbore of the prior disclosed hernia tacks. As shown in FIG. 20, distal section 104 has a pointed distal end 112.

Figure 21:
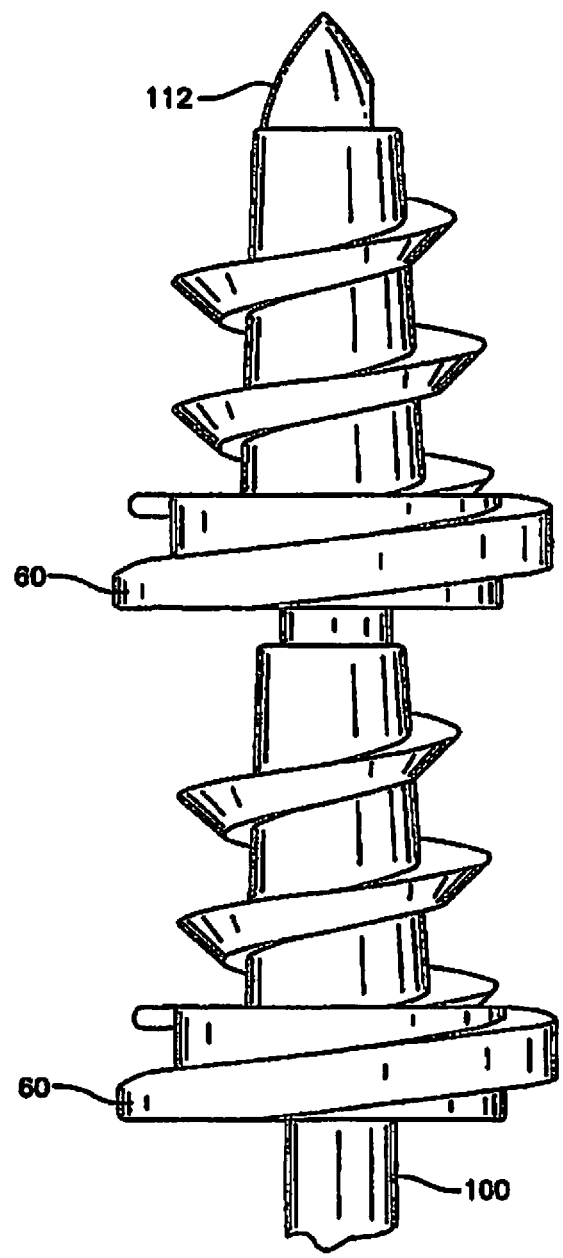
FIG. 21 is a perspective view of the rod of FIG. 18 with multiple tacks.

Referring to FIG. 21, there is illustrated a pair of hernia tacks 60 provided on drive rod 100.

Figure 22:
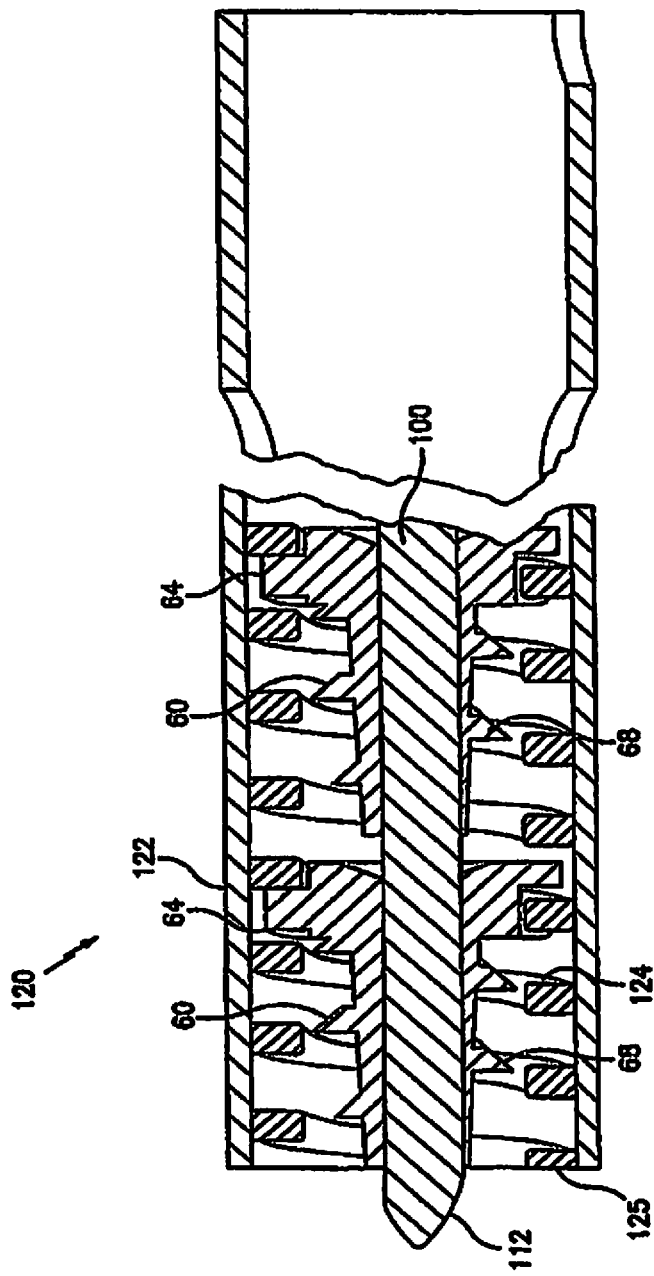
FIG. 22 is a side view, shown in section, of a multi-tack insertion tool.

Referring now to FIG. 22, the distal end of an insertion tool is disclosed for providing multiple surgical tacks 60 to hernia mesh and tissue. Insertion tool 120 includes an outer tube 122 having rotatable drive rod 100 positioned within outer tube 122. As discussed hereinabove, various known handle mechanisms may be provided to rotate drive rod 100 relative to outer tube 122. One known device is disclosed in U.S. Pat. No. 5,582,616 to Bolduc. Drive rod 100 includes pointed distal end 112 to facilitate initially piercing tissue and mesh. As shown, insertion tool 120 includes an inner thread 124 which is configured to engage drive thread 65 of head 64 of a tack 60. Inner thread 124 may be integrally formed in outer tube 122. It should be noted that inner thread 124 may extend completely or partially along the inner surface of outer tube 122. If thread 124 is only provided at the distal end of tube 122, a spring may be used to bias the tacks distally toward thread 124 in tube 122. A distal end 125 of inner thread 124 is positioned flush with the distal end of tube 122. This facilitates reengagement of inner thread 124 with thread 65 of head 64 in the event that tack 60 needs to be withdrawn after installation. As clearly shown, when tacks 60 are loaded into insertion tool 120, tissue thread 66 does not contact inner thread 124 and is not damaged thereby.

Figure 23:
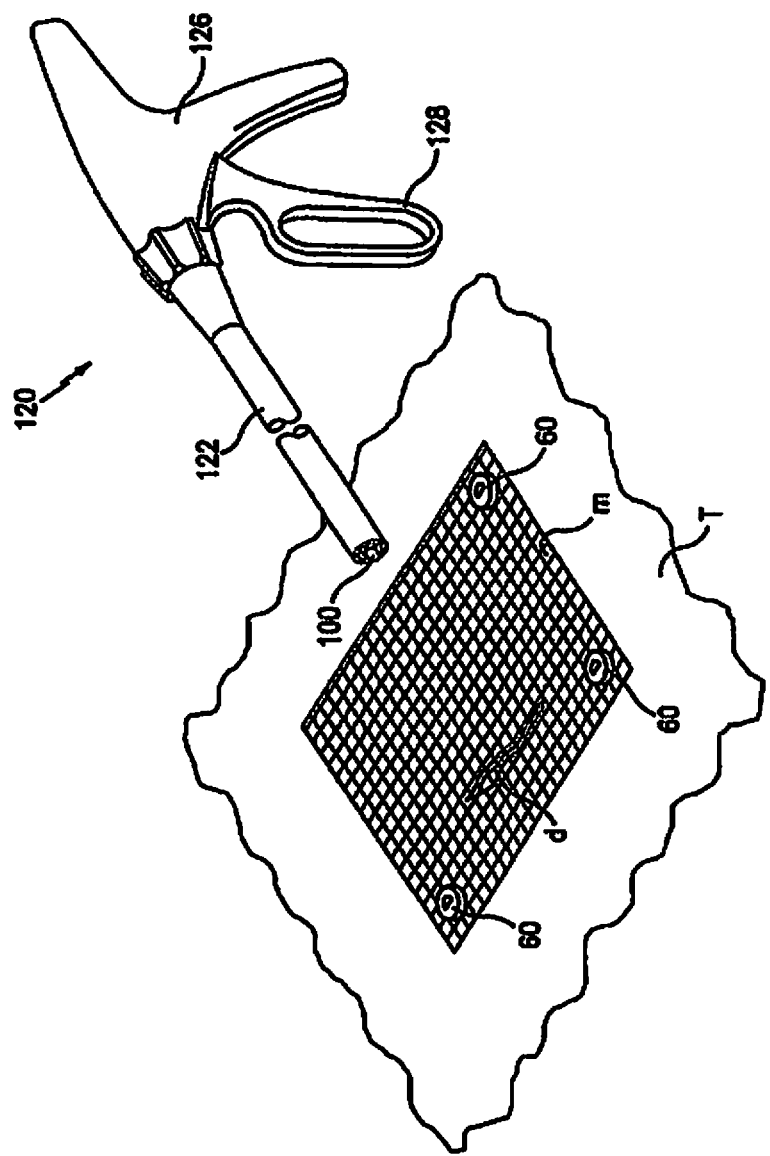
FIG. 23 is a perspective view of an insertion instrument installing tack in mesh and tissue.

Referring to FIG. 23, in use, insertion tool 120 having a handle 126, elongate tube 122 extending distally from handle 126, and an actuator 128 configured to rotate inner rod 100, is positioned such that pointed distal end 112 is against mesh m and underlying tissue t and covering the hernial defect d. Thereafter, a handle mechanism (not shown) may be actuated to rotate drive rod 100 relative to outer tube 212. This causes drive thread 65 of head cap 64 of tack 60 to engage inner thread 124 and drive tack 60 through the mesh m and into tissue t. As noted above, tacks 60 may be biased distally by a spring surrounding drive rod 100 or maybe moved distally by providing inner thread partially, or substantially along the entire length of, outer tube 122.

Figure 24:
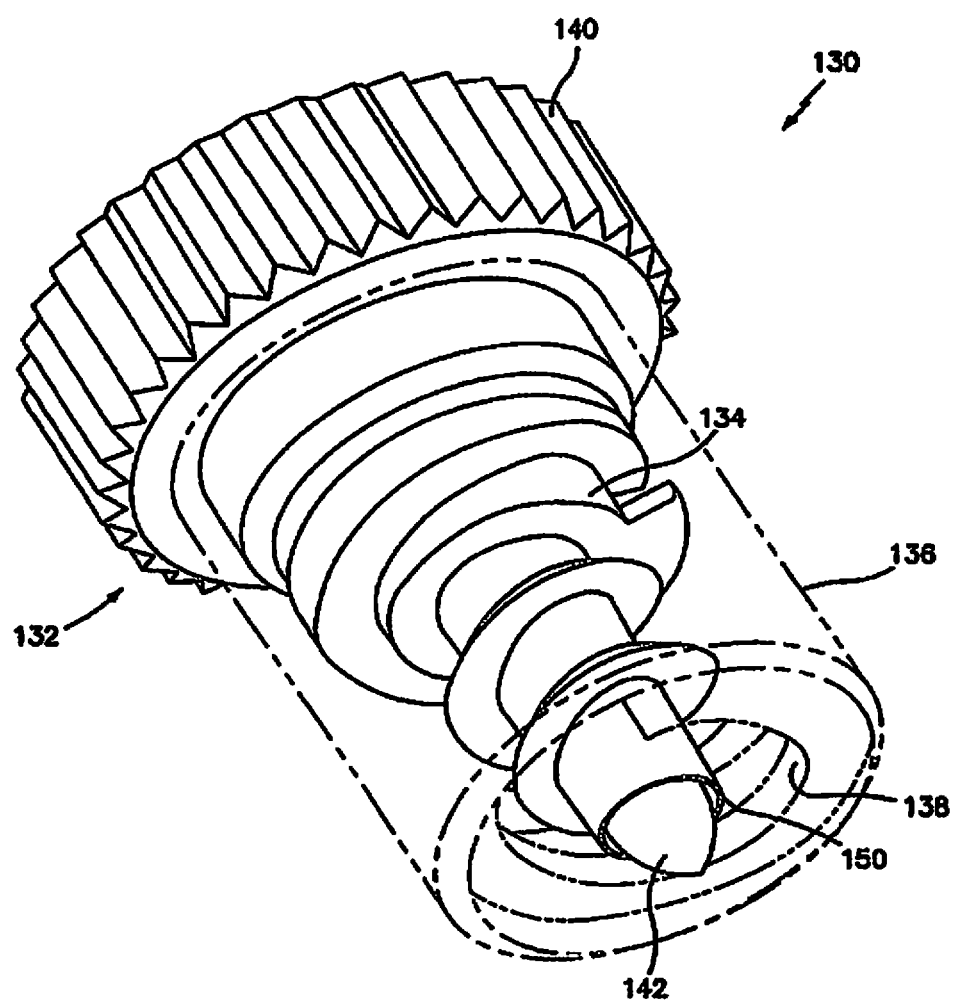
FIG. 24 is a perspective view, with parts shown in phantom, of a display model of a tack and insertion tool.

Referring now to FIG. 24 there is disclosed a display model of the hernia tack and an insertion tool which can be used to show how the actual tack, which is very small on the order of a few millimeters in diameter, is driven out of the insertion tool and into mock tissue and mesh. Display model 130 includes an insertion tool 132 and a tack 134. Insertion tool 130 has an outer tube 136 having an inner thread 138. As with the insertion tools described hereinabove, thread 138 may be integrally formed in outer tube 136 or a separate component affixed to an inner surface of outer tube 136. Additionally, while thread 138 is contemplated as extending completely through outer tube 136, thread 138 may only be provided at the distal end of tube 136 and a spring or other means (not shown) may be provided to bias tacks distally within outer tube 136.

Insertion tool 132 also includes a drive knob 140 having a drive rod 142 extending distally therefrom and through inner tube 136. Drive rod 142 has a pointed distal end to simulate piercing tissue. Drive rod 142 also has arcuate and flat sections configured to engage tack 134 similar to drive rod 100 hereinabove. Tack 134 has a throughbore 144 to receive drive rod 142.

To demonstrate the use of the tack and applier, tack 134 is placed in tube 136 and insertion tool 132 is manipulated to position drive rod 142 in a through bore 150 of tack 134. Knob 140 is then rotated to drive tack 134 out of tube 136.

It will be understood that various modifications may be made to the embodiments disclosed herein. For example, as discussed above, other configurations for the throughbore in the tack, as well as various angles of the tissue threads, may be provided on the tacks. Therefore, the above description should not be construed as limiting, but merely as exemplifications of preferred embodiments. Those skilled in the art will envision other modifications within the scope and spirit of the claims appended hereto.

What is claimed is:

1. A surgical system comprising:
   a tack having a barrel portion with a first thread disposed on the barrel portion; and
   an insertion instrument, the insertion instrument comprising:
      a handle;
      a trigger movably coupled to the handle;
      a tubular member extending distally from the handle and configured for receiving the tack;

a drive member rotatably disposed in the tubular member; and an actuator system operably coupled to the trigger, wherein actuation of the trigger rotates the drive member such that the tack rotates relative to the tubular member and advances longitudinally through the tubular member in a distal direction.

2. The surgical system of claim 1, wherein the tubular member includes internal threading engageable with a portion of the tack.

3. The surgical system of claim 1, wherein at least a portion of the drive member rotatably engages the tack.

4. The surgical system of claim 3, wherein actuation of the actuator system results in rotatable engagement between the drive member and the tack such that the tack rotates relative to the tubular member.

5. The surgical system of claim 1, wherein the tack is stored in the tubular member.

6. The surgical system of claim 5 further comprising a plurality of tacks.

7. The surgical system of claim 6, wherein actuation of the actuator system results in rotatable engagement between a drive member and the tacks such that the tacks rotate relative to the tubular member.

8. A surgical system comprising:
a tack having a barrel portion with a first thread disposed on the barrel portion; and
an insertion instrument, the insertion instrument comprising:
a handle;
a trigger movably coupled to the handle;
a tubular member extending from the handle and configured for receiving the tack;
a drive member rotatably disposed in the tubular member; and
an actuator system operably coupled to the trigger, wherein actuation of the trigger rotates the drive member such that the tack rotates relative to the tubular member and advances longitudinally through the tubular member, wherein the first thread of the tack is spaced from the internal threading of the tubular member such that a gap is defined between the first thread and the internal threading of the tubular member.

9. The surgical system of claim 8, wherein the tack includes a second thread that is separate from the first thread, the first and second threads having the same pitch.

10. A surgical system comprising:
first and second tacks, each tack having a barrel portion with a thread disposed thereon; and
an insertion instrument, the insertion instrument comprising:
a handle;
a trigger movably coupled to the handle;
a tubular member extending from the handle;
a drive rod rotatably disposed in the tubular member, the drive rod configured for engaging the first and second tacks; and
an actuator system operably coupled to the trigger, wherein actuation of the trigger rotates the drive rod such that each tack rotates relative to the tubular member and advances longitudinally through the tubular member away from the handle.

11. The surgical system of claim 10, wherein each tack has a throughbore.

12. A surgical system comprising:
first and second tacks, each tack having a barrel portion with a thread disposed thereon; and
an insertion instrument, the insertion instrument comprising:
a handle;
a trigger movably coupled to the handle;
a tubular member extending from the handle;
a drive rod rotatably disposed in the tubular member, the drive rod configured for engaging the first and second tacks; and
an actuator system operably coupled to the trigger, wherein actuation of the trigger rotates the drive rod such that each tack rotates relative to the tubular member and advances longitudinally through the tubular member, wherein a portion of the drive rod is insertable into the throughbore of each tack.

13. The surgical system of claim 12, wherein the throughbore has a configuration selected from the group consisting of: D-shaped, rectangular, and polygonal.

14. The surgical system of claim 13, wherein the drive rod has a configuration that is complementary to the configuration of the throughbore.

15. A surgical system comprising:
first and second tacks, each tack having a barrel portion with a thread disposed thereon; and
an insertion instrument, the insertion instrument comprising:
a handle;
a trigger movably coupled to the handle;
a tubular member extending from the handle;
a drive rod rotatably disposed in the tubular member, the drive rod configured for engaging the first and second tacks; and
an actuator system operably coupled to the trigger, wherein actuation of the trigger rotates the drive rod such that each tack rotates relative to the tubular member and advances longitudinally through the tubular member, wherein the drive rod has a distal tip configured for penetrating tissue.

* * * * *